United States Patent [19]

Atwal

[11] Patent Number: 5,401,848
[45] Date of Patent: Mar. 28, 1995

[54] INDANE AND QUINOLINE DERIVATIVES

[75] Inventor: Karnail Atwal, Newtown, Pa.

[73] Assignee: E. R. Squibb & Sons, Inc., Princeton, N.J.

[21] Appl. No.: 776,921

[22] Filed: Oct. 15, 1991

Related U.S. Application Data

[63] Continuation-in-part of Ser. No. 618,357, Nov. 26, 1990, abandoned.

[51] Int. Cl.$^6$ ............ C07D 215/46; C07F 9/60; A61K 31/47; A61K 31/68; A61K 31/66

[52] U.S. Cl. ............... 546/153; 546/155; 558/104; 558/418

[58] Field of Search ............ 546/165, 153; 564/104; 558/418; 514/311, 634

[56] References Cited

U.S. PATENT DOCUMENTS

| | | | |
|---|---|---|---|
| 4,575,511 | 3/1986 | Evans et al. | 514/456 |
| 4,631,282 | 12/1986 | Cassidy | 514/354 |
| 5,140,031 | 8/1992 | Atwal et al. | 514/302 |

FOREIGN PATENT DOCUMENTS

| | | |
|---|---|---|
| 2017444 | 11/1990 | Canada . |
| 0168619 | 1/1986 | European Pat. Off. . |
| 0321175 | 6/1989 | European Pat. Off. . |
| 0322251 | 6/1989 | European Pat. Off. . |
| 0344747 | 1/1990 | European Pat. Off. . |
| 0359537 | 3/1990 | European Pat. Off. . |

OTHER PUBLICATIONS

V. A. Ashwood et al., *J. Med. Chem.*, 1986, 29, 2194-2201.

*Primary Examiner*—David B. Springer
*Attorney, Agent, or Firm*—Theodore P. Furman, Jr.; Ellen K. Park

[57] ABSTRACT

Novel indane and quinoline derivatives, useful, for example, as antiischemic agents, having the formula

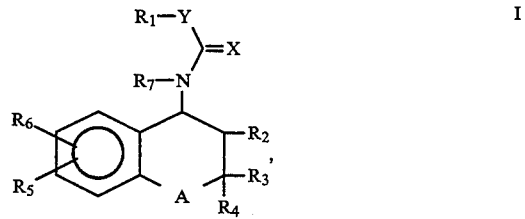

where A, X, $R_1$–$R_7$ are as defined herein, are disclosed.

11 Claims, No Drawings

INDANE AND QUINOLINE DERIVATIVES

This is a continuation-in-part of U.S. Ser. No. 618,357, filed Nov. 26, 1990, now abandoned.

FIELD OF THE INVENTION

The present invention relates to novel potassium channel activators and more particularly is directed to indane and quinoline derivatives having potassium channel activating activity,

SUMMARY OF THE INVENTION

In accordance with the present invention novel potassium channel activators having potassium channel activating activity are disclosed. These compounds used, for example, as cardiovascular and antiischmeic agents have the general formula

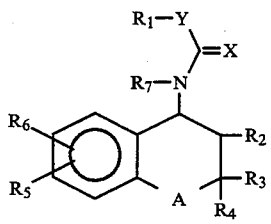

wherein X can be O, S or NCN; provided that when X is O or S, then A is a single bond; or when X is NCN, then A can be a single bond, —$CH_2$—, —$NR_9$—, —S—, —SO— or —$SO_2$—, where $R_9$ is hydrogen or lower alkyl of 1 to 4 carbons;

Y is —$NR_8$, —O—, —S— or

$R_1$ is aryl, arylalkyl, heterocyclo or (heterocyclo)alkyl;

$R_2$ is hydrogen, hydroxy,

$R_3$ and $R_4$ are each independently hydrogen, alkyl or arylalkyl, or, $R_3$ and $R_4$ taken together with the carbon atom to which they are attached form a 5- to 7-membered carbocyclic ring;

$R_5$ is selected from H, alkyl, haloalkyl, alkenyl, alkynyl, cycloalkyl, arylalkyl, cycloalkylalkyl, —CN, —$NO_2$, —COR, —COOR, —CONHR, —$CONR_2$, —$CF_3$, S-alkyl, —SOalkyl, —$SO_2$alkyl,

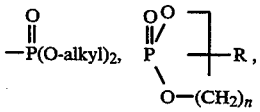

halogen, $OCF_3$, $OCH_2CF_3$, wherein R in each of the above groups can be hydrogen, alkyl, aryl, arylalkyl, cycloalkyl, (cycloalkyl)alkyl or haloalkyl;

$R_6$ is selected from H, alkyl, halo, OH, O-alkyl, amino and substituted amino, O-alkyl, —OCOalkyl, —OCONRalkyl, —NRCOalkyl and NRCOOalkyl, $NRCONR_2$ wherein R in each of the above groups can be hydrogen, alkyl, aryl, arylalkyl, cycloalkyl, (cycloalkyl)alkyl or haloalkyl;

$R_7$ and $R_8$ are each independently selected from hydrogen, alkyl, arylalkyl;

or $R_1$ and $R_8$, or $R_1$ and $R_7$, or $R_7$ and $R_8$ taken together can form a 5- to 7-membered ring, which may further include an aryl group fused to 2 carbon atoms of such 5- to 7-membered ring;

n is 1, 2 or 3; and, $R_{10}$ is hydrogen, hydroxy, alkyl or O-alkyl.

DETAILED DESCRIPTION OF THE INVENTION

The term "alkyl" used in defining various symbols refers to straight or branched chain saturated hydrocarbon radicals having up to eight carbons, preferably from one to five carbons. Similarly, the terms "alkoxy" and "alkylthio" refer to such alkyl groups attached to an oxygen or sulfur.

The term "alkenyl" refers to straight or branched chain hydrocarbon radicals having from two to eight carbons and one double bond, preferably three to five carbons. The term "alkynyl" refers to straight or branched chain hydrocarbon radicals having from two to eight carbons and one triple bond, preferably three to five carbons.

The term "cycloalkyl" refers to saturated carbocyclic rings of 3 to 7 carbon atoms with cyclopropyl, cyclopentyl and cyclohexyl being most preferred.

The term "halo" or "halogen" refers to chloro, bromo, iodo and fluoro.

The term "halo substituted alkyl" refers to such alkyl groups described above in which one or more hydrogens have been replaced by chloro, bromo or fluoro groups such as trifluoromethyl, which is preferred, pentafluoroethyl, 2,2,2-trichloroethyl, chloromethyl, bromomethyl, etc.

The term "aryl" refers to phenyl, 1-naphthyl, 2-naphthyl or mono substituted phenyl, 1-naphthyl, 2-naphthyl wherein said substituent is alkyl of 1 to 4 carbons, alkylthio of 1 to 4 carbons, alkoxy of 1 to 4 carbons, halo, nitro, cyano, hydroxy, amino, —NH—alkyl wherein alkyl is of 1 to 4 carbons, —$N(alkyl)_2$ wherein alkyl is of 1 to 4 carbons, $N(R_{11})COR_{11}'$, $N(R_{11})CO$-haloalkyl, $N(R_{11})CO$-amino, $N(R_{11})CO$-substituted amino, $COR_{11}$, $COOR_{11}$ (wherein $R_{11}$ and $R_{11}'$ are independently H, alkyl, haloalkyl, aryl, arylalkyl) —$CF_3$, —$OCHF_2$,

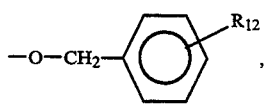

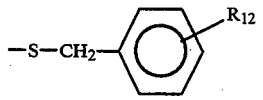

(wherein $R_{12}$ is hydrogen, alkyl of 1 to 4 carbons, alkoxy of 1 to 4 carbons, alkylthio of 1 to 4 carbons, halo, hydroxy or $CF_3$), —O—$CH_2$-cycloalkyl, or —S—$CH_2$-cycloalkyl, and di-substituted phenyl, 1-naphthyl, 2-naphthyl wherein said substituents are selected from methyl, methoxy, methylthio, halo, $CF_3$, nitro, amino, and $OCHF_2$.

Preferred aryl groups include unsubstituted phenyl and monosubstituted phenyl wherein the substituents are nitro, halo, —CF$_3$, alkyl, cyano or methoxy.

The term "heterocyclo" refers to fully saturated or unsaturated rings of 5 or 6 atoms containing one or two O and S atoms and/or one to four N atoms provided that the total number of hetero atoms in the ring is 4 or less. The hetero ring is attached by way of an available atom. Preferred monocyclic hetero groups include 2- and 3-thienyl, 2- and 3-furyl, 2-, 3- and 4-pyridyl, and imidazolyl. The term hetero also includes bicyclic rings wherein the five or six membered ring containing O, S and N atoms as defined above is fused to a benzene ring and the bicyclic ring is attached by way of an available carbon atom. Preferred bicyclic hetero groups include 4, 5, 6, or 7-indolyl, 4, 5, 6, or 7-isoindolyl, 5, 6, 7 or 8-quinolinyl, 5, 6, 7 or 8-isoquinolinyl, 4, 5, 6, or 7-benzothiazolyl, 4, 5, 6 or 7-benzoxazolyl, 4, 5, 6 or 7-benzimidazolyl, 4, 5, 6 or 7-benzoxadiazolyl, and 4, 5, 6 or 7-benzofuranzanyl.

The term heterocyclo also includes such monocyclic and bicyclic rings wherein an available carbon atom is substituted with a lower alkyl of 1 to 4 carbons, lower alkylthio of 1 to 4 carbons, lower alkoxy of 1 to 4 carbons, halo, nitro, keto, cyano, hydroxy, amino, —NH-alkyl wherein alkyl is of 1 to 4 carbons, —N(alkyl)$_2$ wherein alkyl is of 1 to 4 carbons, CF$_3$, or OCHF$_2$ or such monocyclic and bicyclic rings wherein two or three available carbons have substituents selected from methyl, methoxy, methylthio, halo, CF$_3$, nitro, hydroxy, amino and OCHF$_2$.

The term "substituted amino" refers to a group of the formula —NZ$_1$Z$_2$ wherein Z$_1$ is hydrogen, alkyl, cycloalkyl, aryl, arylalkyl, cycloalkylalkyl and Z$_2$ is alkyl, cycloalkyl, aryl, arylalkyl, cycloalkylalkyl or Z$_1$ and Z$_2$ taken together with the nitrogen atom to which they are attached are 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diaryalkyl-1-piperazinyl, 1-pyrrolidinyl, 1-piperidinyl, or 1-azepinyl substituted with alkyl, alkoxy, alkylthio, halo, trifluoromethyl or hydroxy.

The compounds of formula I wherein X is NCN and Y is NR$_8$ can be prepared by reacting a compound of the formula

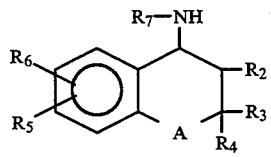

with a thiourea of the formula

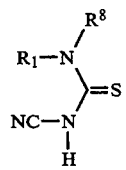

in the presence of a coupling agent, e.g., a carbodiimide, in an organic solvent, e.g., dimethylformamide, tetrahydrofuran, acetonitrile or dichloromethane. If, for example, dicyclohexylcarbodiimide is used it should be employed with an acid source. Preferably, the carbodiimide is of the formula

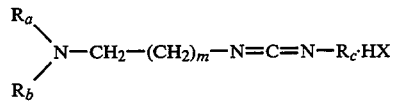

where X is halogen, R$_a$, R$_b$ and R$_c$ are independently alkyl, cycloalkyl, phenyl, phenylalkyl, cycloalkylalkyl or R$_a$ and R$_b$ taken together with the nitrogen atom to which they are attached form 1-pyrrolidinyl, 1-piperazinyl, 4-morpholinyl, 4-thiomorpholinyl, 4-alkyl-1-piperazinyl or 4-phenylalkyl-1-piperazinyl. Most preferably the carbodiimide is 1-(3-dimethylaminopropyl)-3-ethylcarbodiimide hydrochloride.

The thiourea of formula III can be prepared by heating an isothiocyanate of the formula $$R_1N\!=\!C\!=\!S \qquad IV$$

with either monosodium cyanamide, or with cyanamide in the presence of a base, e.g., triethylamine.

The preparation of compounds of formula II can be accomplished using techniques described in the literature. For example, compounds of formula II where A is NH can be prepared using methodology described in WO 85/00602A.

Compounds of formula II where A is S, SO or SO$_2$ can be prepared using methodology described in EP 322-251-A.

Compounds of formula II where A is CH$_2$ can be prepared using methodology described in EP 168-619-A.

Compounds of formula II where A is a single bond can be prepared using methodology described in EP 321-175.

Compounds of formula I where X is O and Y is NR$_8$ can be prepared by reacting a compound of the formula

with 4-nitrophenylchloroformate to provide an intermediate of the formula

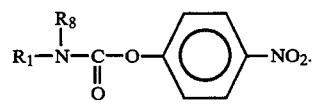

Intermediate VI can thereafter be reacted with the amine of formula II in an organic solvent, such as dimethylformamide, tetrahydrofuran, acetonitrile or dichloromethane to provide the compounds of formula I where X is oxygen and Y is NR$_8$.

Compounds of formula I wherein X is oxygen or sulfur and Y is NR$_8$ (where R$_5$ is hydrogen) can also be prepared from compound of formula II by treatment with an isocyanate or isothiocyanate of the formula $$R_1N\!=\!C\!=\!Z \;(Z\!=\!O, S). \qquad VII$$

Compounds of formula I wherein X and Y are oxygen can be prepared from a compound of formula II by treatment with a chloroformate of the formula

in an organic solvent and in the presence of an amine catalyst.

Compounds of formula I wherein X is oxygen and Y is

can be prepared by reacting a compound of formula II with an acid of the formula

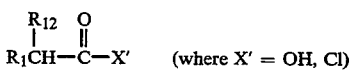

and a carbodiimide or an acyl chloride of formula XIX in an organic solvent and a base such as triethylamine and pyridine.

Compounds of formula I wherein X is sulfur can be prepared by treating compounds of formula I wherein X is oxygen with Lawesson's reagent or with $P_4S_{10}$ in organic solvents such as tetrahydrofuran and toluene.

If any of the R's in the above reactions contain one or more hydroxy or amino groups, heterocyclo wherein the heterocyclo ring contains an NH such as imidazolyl then the hydroxyl, amino or mercaptan function should be protected during the reaction. Suitable protecting groups include benzyloxycarbonyl, t-butoxycarbonyl, benzyl, benzhydryl, etc. The protecting group is removed by standard means following completion of the reaction.

The compounds of the present invention can have asymmetric centers at ring carbons. Also, any one of the R's can have an asymmetric carbon. Consequently, compounds of formula I can exist in diastereomeric forms or in mixtures thereof. The above described process can utilize racemates, enantiomers or diastereomers as starting materials. When diastereomeric products are prepared, they can be separated by conventional chromatographic or fractional crystallization methods.

The compounds of the present invention wherein $R_7$ is hydrogen, Y is $NR_8$ and $R_8$ is hydrogen, can exist as a mixture of tautomers represented by the following structures. The tautomeric products are obtained in relative amounts that differ from compound to compound. All forms are included in the scope of formula I.

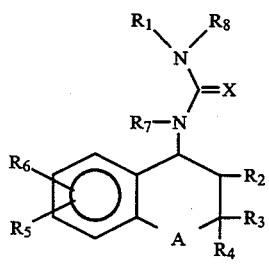

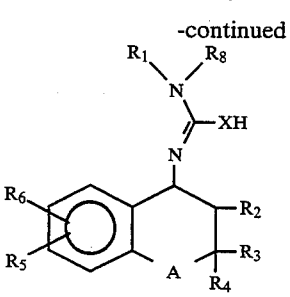

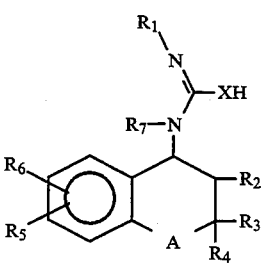

Tautomers of formula I similar to I' and I'' are also possible wherein Y is O, S and

and are also included in the scope of this invention.

The compounds of formula I and the pharmaceutically acceptable salts act as potassium channel activators. Thus, compounds of the present invention are useful cardiovascular agents, e.g. as anti-arrhythmic agents and antiischemic agents.

As described previously, compounds of formula I are particularly useful as antiischemic agents since they have been found to possess little or no antihypertensive activity. Thus, compounds of formula I are useful for the treatment of ischemic conditions, e.g. myocardial ischemia, cerebral ischemia, lower limb ischemia and the like. Preferred are those compounds of formula I wherein $R_1$ is aryl. These compounds appear to be "selective" antiischemic agents, i.e., they have little or no vasodilatory action in normal tissue. By little or no vasodilatory action is meant that these agents have $IC_{50}$ (rat aorta) values greater than the known potassium channel activator, cromakalim. Preferably, these compounds have $IC_{50}$ (rat aorta) values >10 times that of cromakalim, and most preferably >50 times that of cromakalim. The selectivity, i.e., antiischemic activity with little or no antihypertensive activity, means that in the treatment of, for example, ischemic heart, these compounds are less likely to cause coronary steal, profound hypotension and coronary underperfusion.

Thus, for example, by the administration of a composition containing one (or a combination) of the compounds of this invention, ischemic conditions of a mammalian (e.g., human) host are reduced. A single dose, or preferably two to four divided daily doses, provided on a basis of about 0.001 to 100 mg per kilogram of body weight per day, preferably from about 0.1 to about 25 mg per kilogram per day, is appropriate to reduce ischemic conditions. The substance is preferably administered orally, but parenteral routes, such as the subcutaneous, intramuscular, or intravenous routes or any other convenient delivery system, such as inhalation or intranasal solutions or transdermal patches, can also be employed. The above doses are also suitable for the other cardiovascular and non-cardiovascular uses.

As a result of the potassium channel activating activity of compounds of this invention, these compounds are also useful in the treatment of cardiovascular disorders. For example, compounds of the present invention are useful as therapy for congestive heart failure, as anti-anginal agents, as anti-fibrillatory agents, as thrombolytic agents and in limiting myocardial infarction.

Compounds of the present invention are additionally expected to be useful in the treatment of central nervous system disorders (e.g., Parkinsonism, as anti-tremor agents, epilepsy).

The compounds of this invention can also be formulated in combination with a diuretic such as, chlorothiazide, hydrochlorothiazide, flumethiazide, hydroflumethiazide, bendroflumethiazide, methylchlothiazide, trichloromethiazide, polythiazide or benzthiazide as well as ethacrynic acid, tricrynafen, chlorthalidone, furosemide, musolimine, bumetanide, triamterene, amiloride and spironolactone and salts of such compounds, angiotensin converting enzyme inhibitors such as captopril, zofenopril, fosinopril, enalapril, ceranopril, cilazopril, delapril, pentopril, quinapril, ramipril, lisinopril, and salts of such compounds, thrombolytic agents such as tissue plasminogen activator (tPA), recombinant tPA, streptokinase, urokinase, prourokinase, and anisoylated plasminogen streptokinase activator complex (APSAC, Eminase, Beecham Laboratories), or calcium channel blocking agents such as nifedipine or diltiazem. Such combination products if formulated as a fixed dose employ the compounds of this invention within the dose range described above and the other pharmaceutically active agent within its approved dose range.

The compounds of formula I, and combinations thereof, can be formulated, as described above, in compositions such as tablets, capsules or elixirs for oral administration, in sterile solutions or suspensions for parenteral administration, and may also be administered via transdermal patch or nasal inhalation solutions. About 10 to 500 milligrams of a compound of formula I is compounded with physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Preferred compounds are those wherein
A is a single bond, $CH_2$;
$R_1$ is aryl, arylmethyl;
$R_2$ is H, trans-OH;
$R_3$ and $R_4$ are each methyl;
$R_5$ is H;
$R_5$ is CN, $NO_2$;
$R_7$ is H;
X is O, S, NCN;
Y is $NR_8$, $CH_2$; and,
$R_5$ is H.

Most preferred are those compounds wherein
A is a single bond;
$R_1$ is phenyl, phenylmethyl;
$R_2$ is trans-OH;
$R_3$ and $R_4$ are each methyl;
$R_5$ is H;
$R_5$ is CN, $NO_2$;
$R_7$ is H;
X is O, NCN;

Y is $NR_8$; and,
$R_8$ is H.

Specific embodiments of the present invention are described hereinafter in the following examples.

EXAMPLE 1

(trans)-N''-Cyano-N-(2-hydroxy-3,3-dimethyl-6-nitro-1-indanyl)-N'-phenylguanidine

A. 4-Methyl-4-phenyl-2-pentanone

To a slurry of aluminum chloride (40.0 g, 0.3 mole) in benzene (90 ml) maintained at 10° C. under argon was added dropwise mesityl oxide (19.63 g, 0.2 mole). Upon completion of the addition the reaction was stirred at room temperature for 1.5 hours. The reaction mixture was poured onto ice/10% HCl (350 g). The organic layer was separated and the aqueous layer was extracted with ethyl acetate (100 ml). The combined organics were washed with distilled water, saturated sodium hydrogen carbonate solution, saturated sodium chloride solution and dried over sodium sulfate. The solvent was evaporated under vacuum and the crude product (31.6 g) was vacuum distilled (b.p.=107° C. at 3.0 mmHg) to obtain 24.5 g of the title A compound as a colorless oil. $^1$H NMR (CDCl$_3$) δ 7.38–7.19 (m, 5H), 2.74 (s, 2H), 1.80 (s, 3H), 1.43 (s, 6H). $^{13}$C NMR (CDCl$_3$) δ 207.94, 148.16, 128.26, 125.95, 125.46, 56.96, 37.29, 31.76, 28.88.

B. 3-Methyl-3-phenylbutanoic acid

To a solution of sodium hydroxide (47.2 g, 1.18 mmol) in ice/water (270 g) maintained at 4°–5° C. was added bromine (68.7 g, 0.43 mole) followed by the title A compound (23.7 g, 0.135 mole). The reaction was stirred 18 hours at room temperature. The crude reaction mixture was extracted with carbon tetrachloride (discarded), acidified to pH 1–2 with concentrated hydrochloric acid solution and extracted with ethyl acetate. The combined organics were washed with saturated sodium chloride solution, dried over sodium sulfate and evaporated in vacuo to obtain 22.5 g of the title B compound as an off-white solid. This was used in the next step without further purification. $^1$H NMR (CDCl$_3$) δ 7.88–7.16 (m, 5H), 2.64 (s, 2H), 1.46 (s, 6H). $^{13}$C NMR (CDCl$_3$) δ 177.87, 147.96, 128.23, 126.04, 125.38, 47.97, 36.97, 28.79.

C. 3,3-Dimethyl-1-indanone

To a solution of the title B compound (17.1 g, 95.5 mmoles) in benzene (70 ml) was added phosphorous pentachloride (23.0 g, 0.11 mole, 1.15 eq.) portionwise with cooling. Upon completion of the addition, the reaction mixture was refluxed for 30 minutes and cooled to room temperature. Aluminum chloride (13.1 g, 98.3 mmoles) was added in increments and the reaciton was heated at reflux for 30 minutes. The reaction mixture was poured onto ice; the oily layer was separated and the aqueous layer was extracted with ethyl acetate. The combined organics were washed with 5% hydrochloric acid solution, saturated sodium hydrogen carbonate solution, saturated sodium chloride solution and dried over anhydrous magnesium sulfate. The solvent was evaporated in vacuo and the crude product (14.3 g) was vacuum distilled (b.p.=103° C. at 2.3 mmHg) to obtain 9.98 g of the title C compound as a colorless oil. $^1$H NMR (CDCl$_3$) δ 7.70 (d, J=7.62 Hz, 1H), 7.61 (m, 1H), 7.50 (d, J=7.62 Hz, 1H), 7.39 (m, 1H), 2.59 (s, 2H), 1.42

(s, 6H). $^{13}$C NMR (CDCl$_3$) δ 205.78, 163.76, 135.26, 134.88, 127.34, 123.45, 123.28, 52.93, 38.47, 29.92, 29.48.

D. 1,1-Dimethyl-5-nitro-3-indanone

A mixture of nitric acid (90% fuming, 35 ml) and urea (0.17 g) was cooled to −10° C. and purged with air for 20 minutes; the title C compound (8.68 g, 54.2 mmoles) was added and the reaction was stirred for 2 hours at −10° C. to 5° C. The reaction mixture was poured into ice/water and extracted with ethyl acetate. The combined extracts were washed with distilled water, saturated sodium hydrogen carbonate solution, saturated sodium chloride solution, and dried over anhydrous magnesium sulfate. The solvent was evaporated under vacuum to obtain 10.0 g of a yellow solid. The crude product was recrystallized from methanol in two crops to obtain 8.08 g of the title D compound as yellow needles. $^1$H NMR (CDCl$_3$) δ 8.49 (d, J=1.76 Hz, 1H), 8.45 (d, J=2.34 Hz, 1H), 7.69 (d, J=8.21 Hz, 1H), 2.71 (s, 2H), 1.49 (s, 6H). $^{13}$C NMR (CDCl$_3$) δ 203.36, 169.15, 147.84, 136.29, 129.24, 124.84, 118.82, 52.96, 39.13, 29.63.

E. 1,1-Dimethyl-5-nitro-indan-3-ol

A solution of the title D compound (6.75 g, 32.9 mmoles) in methanol (200 ml) was cooled to 0° and treated with potassium borohydride (1.77 g, 32.9 mmoles). The reaction mixture was stirred one hour at 0°–10° C. and concentrated under vacuum. The residue was partitioned between ethyl acetate and distilled water; the aqueous phase was extracted with ethyl acetate. The combined organics were washed with saturated sodium chloride solution, dried over anhydrous magnesium sulfate and evaporated in vacuo to obtain 6.61 g of the title E compound as a yellow solid. The crude product was used in the next step without further purification. $^1$H NMR (CDCl$_3$) δ 8.12 (s, 1H), 8.07 (d, J=8.21, 1H), 7.22 (d, J=8.80 Hz, 1H), 5.24 (m, 1H), 2.39 (dd, J=7.04 and 12.90 Hz, 1H), 1.85 (dd, J=7.04 and 12.90 Hz, 1H), 1.35 (s, 3H), 1.17 (s, 3H). $^{13}$C NMR (CDCl$_3$) δ 159.16, 147.49, 145.36, 124.14, 122.99, 119.79, 73.31, 51.69, 42.56, 29.40, 29.23.

F. 1,1-Dimethyl-5-nitro-2-indene

A solution of the title E compound (6.58 g, 31.8 mmoles) and p-toluene sulfonic acid (0.5 g) in benzene (165 ml) was refluxed for 18 hours while removing water azeotropically. The reaction mixture was cooled, washed with 2N sodium hydroxide, saturated sodium hydrogen carbonate solution, saturated sodium chloride solution and dried over anhydrous magnesium sulfate. The solvent was recovered under vacuum to obtain 5.91 g of the title F compound as an off-white solid. The reaction product was used in the next step without further purification. $^1$H NMR (CDCl$_3$) δ 8.03 (s, 1H), 8.00 (s, 1H), 7.33 (d, J=7.62 Hz, 1H), 6.59 (d, J=5.86 Hz, 1H), 6.47 (d, J=5.86 Hz, 1H), 1.26 (s, 6H). $^{13}$C NMR (CDCl$_3$) δ 160.22, 150.06, 147.44, 143.92, 126.64, 121.36, 120.74, 116.14.

G. 1,1-Dimethyl-2,3-epoxy-5-nitro-indane

A solution of the title F compound (4.5 g, 23.8 mmoles) in dichloromethane (100 ml) cooled to 0° C. was treated with m-chloroperbenzoic acid (80%, 5.64 g, 26.2 mmoles, 1.1 eq.) and stirred 18 hours at room temperature. The solvent was recovered under vacuum and the residue was partitioned between ethyl acetate and 10% sodium bisulfite. The organic layer was washed with 2N sodium hydroxide solution (until the wash was basic), saturated sodium chloride solution and dried over anhydrous magnesium sulfate. The solvent was evaporated in vacuo to obtain 4.84 g of the title G compound as a white solid. The product was used in the next step without further purification. $^1$H NMR (CDCl$_3$) δ 8.23 (d, J=1.76 Hz, 1H), 8.11 (dd, J=2.35 and 8.21Hz, 1H), 7.24 (d, J=8.21 Hz, 1H), 4.26 (d, J=2.93 Hz, 1H), 3.73 (d, J=2.93, 1H), 1.38 (s, 3H), 1.20 (s, 3H). $^{13}$C NMR (CDCl$_3$) δ 160.22, 147.00, 141.24, 124.43, 120.45, 120.31, 64.90, 56.50, 44.43, 26.69, 22.08.

H. (trans)-3-Amino-1,1-dimethyl-2-hydroxy-5-nitroindane

A solution of the title G compound (4.80 g, 23.4 mmoles) in a mixture of ethanol (24 ml), tetrahydrofuran (24 ml) and saturated ammonium hydroxide solution (24 ml) was heated in a thickwalled glass pressure bottle at 55°–60° C. for 24 hours. The volatiles were evaporated in vacuo to obtain 5.16 g of a green solid. The crude material was recrystallized from hot ethanol in two crops to provide 4.40 g of the title H compound as a yellow crystalline solid. $^1$H NMR (DMSO-d$_6$) δ 8.14 (s, 1H), 8.10 (d, J=8.21 Hz, 1H), 7.44 (d, J=8.21 Hz, 1H), 3.95 (d, J=8.21 Hz, 1H), 3.53 (d, J=8.80 Hz, 1H), 1.30 (s, 3H), 1.02 (s, 3H). $^{13}$C NMR (DMSO-d$_6$) δ 156.67, 146.91, 145.36, 123.41, 122.87, 118.89, 88.40, 59.40, 44.02, 25.22, 22.37.

I. (trans)-N''-Cyano-N-(2-hydroxy-3,3-dimethyl-6-nitro-1-indanyl)-N'-phenylguanidine A solution of the title H compound (1.0 g, 4.5 mmoles), N-cyano-N'-phenylthiourea (1.04 g, 5.85 mmoles) and 1-(3-dimethylaminopropyl)-2ethylcarbodiimide hydrochloride (1.12 g, 5.85 mmoles) in N,N-dimethylformamide (8.5 ml) was stirred at room temperature under argon for three hours. The reaction mixture was partitioned between ethyl acetate and 1N hydrochloric acid solution. The aqueous layer was extracted with ethyl acetate. The combined organics were washed with saturated sodium hydrogen carbonate solution, saturated sodium chloride solution, dried over sodium sulfate and evaporated in vacuo to obtain 0.58 g of an off-white solid. The aqueous hydrochloric acid phase was neutralized with sodium hydrogen carbonate and extracted with ethyl acetate to afford an additional 0.44 g of crude product. The product fractions were combined, recrystallized from methanol/isopropanol and triturated with isopropyl ether to obtain 0.70 g of the title compound as an off-white solid, m.p. 249°–251° C. $^1$H NMR (DMSO-d$_6$) δ 9.39 (s, 1H), 8.16 (d, J=7.63 Hz, 1H), 7.94 (s, 1H), 7.79 (d, J=8.21 Hz, 1H), 7.52 (d, J=8.21 Hz, 1H), 7.36 (m, 4H), 7.16 (m, 1H), 5.81 (broad s, 1H), 5.24 (m, 1H), 4.06 (m, 1H), 1.31 (s, 3H), 1.08 (s, 3H). $^{13}$C NMR (DMSO-d$_6$) δ 158.86, 156.64, 146.85, 140.92, 137.61, 129.03, 124.77, 123,99, 123.62, 123.50, 118.63, 116.99, 83.82, 60.06, 43.99, 24.90, 22.51.

Analysis calc'd for $C_{19}H_{19}N_5O_3$: C, 62.46; H, 5.24; N, 19.17; Found: C, 62.28; H, 5.17; N, 19.06.

EXAMPLE 2

(trans-)N-(2-Hydroxy-3,3-dimethyl-6-nitro-1-indanyl)-N'-phenylurea

To a solution of trans-3-amino-1,1-dimethyl-2-hydroxy-5-nitro indane (0.75 g, 3.37 mmoles, as prepared in part H of Example 1) in refluxing ethanol (6 ml)

was added phenyl isocyanate (0.40 g, 3.37 mmoles). The reaction mixture was heated at reflux for 3 hours and cooled to room temperature. The product, which had precipitated from solution, was collected via suction filtration and washed with isopropyl ether. In this manner 0.82 g of the title compound was obtained as a white solid, m.p. 194°–195° C. $^1$H NMR (DMSO-$d_6$) δ 8.66 (s, 1H), 8.16 (d, J=8.79 Hz, 1H), 7.94 (s, 1H), 7.51 (m, 3H), 7.28 (m, 2H), 6.95 (m, 1H), 6.73 (d, J=7.62 Hz, 1H), 5.67 (d, J=5.28 Hz, 1H), 5.00 (t, J=8.21 Hz, 1H), 3.86 (dd, J=5.86 and 8.79 Hz, 1H), 1.36 (s, 3H), 1.09 (s, 3H). $^{13}$C NMR (DMSO-$d_6$) δ 156.53, 155.75, 146.91, 142.36, 140.26, 128.74, 123.96, 123.47, 121.37, 118.63, 117.91, 84.71, 57.70, 44.11, 25.07, 22.42.

Analysis calc'd for $C_{18}H_{19}N_3O_4$: C, 63.33; H, 5.61; N, 12.31; Found: C, 63.21; H, 5.62; N, 12.38.

EXAMPLE 3

(trans)-N-(2-Hydroxy-3,3-dimethyl-6-nitro-1-indanyl)-N'-(phenylmethyl)urea

A solution of trans-3-amino-1,1-dimethyl-2-hydroxy-5-nitro indane (0.75 g, 3.37 mmoles, as prepared in part H of Example 1) and benzyl isocyanate (0.45 g, 3.37 mmoles) in ethanol (6 ml) was heated at reflux for three hours and cooled to room temperature. The reaction product, which had precipitated from solution was collected by suction filtration and dried under vacuum to afford 1.13 g of the title compound as a pure white solid, m.p. 202°–204° C. $^1$H NMR (DMSO-$d_6$) δ 8.14 (dd, J=2.34 and 8.21 Hz, 1H), 7.91 (s, 1H), 7.50 (d, J=8.21 Hz, 1H), 7.39–7.25 (m, 5H), 6.61 (m, 1H), 5.63 (d, J=5.28 Hz, 1H), 4.93 (dd, J=8.21 and 8.79 Hz, 1H), 4.34 (d, J=5.68 Hz, 2H), 3.79 (dd, J=5.87 and 8.79 Hz, 1H), 1.32 (s, 3H), 1.06 (s, 3H). $^{13}$H NMR (DMSO-$d_6$) δ 158.63, 156.50, 146.85, 142.88, 140.81, 128.25, 127.01, 126.61, 123.87, 123.33, 118.66, 84.74, 57.93, 44.05, 44.07, 25.04, 22.42.

Analysis calc'd for $C_{19}H_{21}N_3O_4$: C, 64.21; H, 5.96; N, 11.82; Found: C, 64.07; H, 5.92; N, 11.66.

EXAMPLE 4

(trans)-N-(6-Bromo-1,2,3,4-tetrahydro-3-hydroxy-2,2-dimethyl-4-quinolinyl)-N''-cyano-N'-phenylguanidine

A. 3-Chloro-3-methylbutyne

A mixture of 2-methyl-3-butyne-2-ol (84.1 g, 100 mmol) (98.8 ml), hydroquinone (1.0 g), calcium chloride (110 g, 100 mmol) in concentrated hydrochloric acid (420 ml) was stirred vigorously (overhead stirrer) while keeping the temperature at 20° C. by ice. The reaction mixture was stirred for one hour at room temperature. The organic layer was then separated and dried over anhydrous potassium carbonate. Removal of drying agent and distillation at atmospheric pressure gave the desired product (47.0 g), b.p. 76°–80° C. $^1$H NMR (CDCl$_3$) δ 2.6 (s, 1H), 1.85 (s, 6H).

B. 4-Bromo-N-(1,1-dimethyl-2-propynyl)aniline

The title A compound (48.0 g, 470 mmol) was added dropwise to a vigorously stirred mixture of 4-bromoaniline (51.2 g, 298 mmol), triethylamine (41.0 g, 406 mmole), copper(I)chloride (0.8 g), copper bronze (0.8 g) in aqueous ethyl ether (40/200 ml), while maintaining the temperature at 15°–22° C. The reaction mixture was stirred at room temperature for 4 hours. It was then poured into aqueous ethyl ether (100/200 ml). The organic layer was separated and washed with water (100 ml), brine (100 ml) and dried over potassium carbonate and potassium hydroxide. Removal of drying agent and evaporation of solvent gave a brown oil which was distilled in vacuo to give the title B compound (70.0 g), b.p. 120°–125° C. at 0.1 mm. $^1$H NMR (CDCl$_3$) δ 7.26 (d, J=9.0 Hz, 2H), 6.80 (d, J=9.0 Hz, 2H), 3.6 (s, 1H), 2.4 (s, 1H), 1.58 (s, 6H). $^{13}$C NMR (CDCl$_3$) δ 144.6, 131.6, 118.1, 110.8, 70.9, 40.1, 30.4.

C. 6-Bromo-2,2-dimethyl-2H-1-dihydroquinoline

The title B compound (70.0 g, 295 mmol) was dissolved in dioxane (250 ml) and treated with copper(I)-chloride (43.5 g). The reaction mixture was heated at reflux temperature for four hours under nitrogen. The reaction mixture was cooled and diluted with ethyl ether (300 ml). It was then washed with water (3×100 ml), brine and dried over anhydrous magnesium sulfate. This was concentrated in vacuo and purified by flash chromatography eluting with hexane/ethyl acetate mixture (8/2) to give 70.0 g of the title C compound. $^1$H NMR (CDCl$_3$) δ 7.06 (m, 2H), 6.32 (d, J=8.0 Hz, 1H), 6.22 (d, J=10.0 Hz, 1H), 5.54 (d, J=10.0 Hz, 1H), 1.34 (s, 6H). $^{13}$C NMR (CDCl$_3$) δ 142.0, 132.0, 130.8, 128.8, 122.6, 121.7, 114.2, 108.3, 52.2, 31.0.

D. 1-Acetyl-6-bromo-2,2-dimethyl-1,2-dihydroquinoline

Acetyl chloride (12 ml) was added dropwise to a stirred solution of the title C compound (19.8 g, 83.3 mmol) and N,N-dimethylaniline (24 ml) in methylene chloride (200 ml) at 0° C. The reaction mixture was stirred further for 24 hours at room temperature and then poured into water (100 ml). The organic layer was separated and washed successively with 1N hydrochloric acid, 1N sodium hydrogen carbonate solution, water and brine and dried over anhydrous magnesium sulfate. Removal of drying agent and evaporation of solvent gave the crude product as a gum (22.4 g).

$^1$H NMR (CDCl$_3$) δ 7.26 (d, J=9.0 Hz, 1H), 7.16 (s, 1H), 6.68 (d, J=8.0 Hz, 1H), 6.25 (d, J=10.0 Hz, 1H), 5.73 (d, J=10.0 Hz, 1H), 2.16 (s, 3H), 1.54 (s, 6H). $^{13}$C NMR (CDCl$_3$) δ 172.1, 140.3, 135.6, 129.6, 129.0, 128.4, 124.6, 121.4, 117.0, 58.3, 26.2, 25.8.

E. 1-Acetyl-3,6-dibromo-2,2-dimethyl-1,2,3,4-tetrahydroquinolin-4-ol

N-Bromosuccinimide (16.0 g, 89.0 mmol) was added to a vigorously stirred solution of the title D compound (22.4 g, 80.0 mmol) in 10% aqueous dimethyl sulfoxide (150 ml) at 0° C. The mixture was stirred for one hour at room temperature, and then diluted with water (100 ml) and extracted with ethyl acetate (3×150 ml). The organic extracts were washed with water, brine, and dried over anhydrous magnesium sulfate. Removal of drying agent and evaporation of solvent gave the title E compound as a gum (30.0 g). $^1$H NMR (CDCl$_3$) δ 7.73 (d, J=3.0 Hz, 1H), 7.37 (dd, J=2.0 & 7.0 Hz, 1H), 6.84 (d, J=9.0 Hz, H), 4.79 (d, J=9.0 Hz, 1H), 3.90 (d, J=9.0 Hz, 1H), 2.76 (d, J=5.0 Hz, 1H), 2.13 (s, 3H), 1.73 (s, 3H), 1.71 (s, 3H). $^{13}$C NMR (CDCl$_3$) δ 172.2, 135.8, 134.9, 130.9, 130.7, 128.4, 128.2, 126.5, 126.4, 118.9, 61.3, 26.4, 26.0, 22.8.

F.
1-Acetyl-6-bromo-3,4-epoxy-2,2-dimethyl-1,2,3,4-tetrahydroquinoline

A mixture of the title E compound (30.0 g, 80.0 mmol) and potassium hydroxide pellets (25.0 g, 438 mmol) in ethyl ether (500 ml) was vigorously stirred at room temperature for 72 hours. The solution was filtered and mother liquor was concentrated in vacuo to give the title F compound (23.0 g). $^1$H NMR (CDCl$_3$) δ 7.51 (d, J=2.0 Hz, 1H), 7.37 (dd, J=2.0 & 6.0 Hz, 1H), 6.71 (d, J=8.0 Hz, 1H), 3.78 (d, J=4.0 Hz, 1H), 3.40 (d, J=4.0 Hz, 1H), 2.09 (s, 3H), 1.89 (s, 3H), 1.18 (s, 3H). $^{13}$C NMR (CDCl$_3$) δ 173.3, 136.9, 132.0, 131.8, 128.0, 126.9, 117.6, 66.76, 56.1, 51.2, 26.4, 25.6, 22.4.

G.
1-Acetyl-6-bromo-3-hydroxy-4-amino-2,2-dimethyl-1,2,3,4-tetrahydroquinoline A solution of the title F compound (18.0 g, 61.0 mmol) in ethanol (150 ml) was treated with concentrated ammonium hydroxide (150 ml) and heated at reflux for 24 hours. It was then concentrated in vacuo and triturated with ethyl ether to give the title G compound as a solid (14.0 g). $^1$H NMR (DMSO-d$_6$) δ 8.07 (d, J=9.0 Hz, 1H), 7.01 (d, J=8.0 Hz, 1H), 6.94 (s, 1H), 6.94 (s, 1H), 6.43 (d, J=8.0 Hz, 1H), 5.9 (s, 1H), 5.07 (s, 1H), 4.71 (t, J=9.0 & 10.0 Hz, 1H), 3.33 (m, 2H), 1.92 (s, 3H), 1.16 (s, 3H), 1.06 (s, 3H). $^{13}$C NMR (CDCl$_3$) δ 170.2, 143.3, 130.0, 129.8, 123.2, 115.5, 106.2, 73.5, 53.6, 50.3, 27.4, 23.0, 20.5.

H.
6-Bromo-3-hydroxy-4-amino-2,2-dimethyl-1,2,3,4-tetrahydroquinoline

To a solution of the title G compound (20.0 g, 64.1 mmol) in dioxane (100 ml) was added concentrated sulfuric acid (20 g) in water (50 ml) and the reaction mixture was heated under reflux for 16 hours. Dioxane was distilled off and the reaction mixture was diluted with water (50 ml), basified to pH 13 by addition of 10N sodium hydroxide, and extracted with ethyl acetate (3×150 ml). The combined organic layers were washed with water and dried over anhydrous magnesium sulfate. It was concentrated in vacuo and triturated with isopropyl ether to give the title H compound as a solid (13.0 g). $^1$H NMR (DMSO-d$_6$) δ 7.55 (s, 1H), 7.25 (dd, J=2.0 & 6.0 Hz, 1H), 6.48 (d, J=8.0 Hz, 1H), 3.77 (d, J=10.0 Hz, 1H), 3.40 (d, J=10.0 Hz, 1H), 2.60 (broad singlet, 3H), 1.47 (s, 3H), 1.26 (s, 3H). $^{13}$C NMR (CDCl$_3$) δ 171.9, 142.3, 130.1, 129.8, 115.2, 107.3, 75.5, 53.5, 50.8, 26.7, 22.4, 19.9.

I.
(trans)-N-(6-Bromo-1,2,3,4-tetrahydro-3-hydroxy-2,2-dimethyl-4-quinolinyl)-N''-cyano-N'-phenylguanidine The solution of N-cyano-N'-phenylthiourea (4.3 g, 24.2 mmol) and the title H compound (5.0 g, 18.6 mmol) in dimethylformamide (30 mL) under argon was treated with 1-(3-dimethylaminopropyl)-2-ethylcarbodiimide hydrochloride (4.6 g, 24.2 mmol). The reaction was stirred at room temperature for 2 hours and then partitioned between 1N hydrochloric acid and ethyl acetate. The aqueous phase was reextracted with ethyl acetate and the combined extracts were washed with water, sodium bicarbonate and brine. After drying over anhydrous magnesium sulfate, the solvent was evaporated and the residue was flash chromatographed on silica gel eluting with a mixture of hexanes/ethyl acetate (1:1/21, 1:2/21), ethyl acetate (21) to yield the title compound (3.4 g), m.p. 232°–233° C. $^1$H NMR (DMSO-d$_6$) δ 9.2 (s, 1H), 7.64 (d, J=9.0 Hz, 1H), 7.40 (m, 6H), 7.16 (m, 1H), 6.53 (d, J=8.8 Hz, 1H), 6.0 (s, 1H), 5.6 (br s, 2H), 4.92 (t, J=9.0 Hz, 1H), 3.6 (m, 1H), 1.27, 1.10 (s, 3H each). $^{13}$C NMR (DMSO-d$_6$) δ 159.1, 143.2, 137.8, 130.2, 129.6, 128.9, 124.3, 122.9, 122.2, 117.2, 115.5, 106.0, 73.0, 53.8, 27.2, 20.5. IR (KBr) 3419.2 2968.0, 2927.7, 2174.7, 1581.5, 1489.6, 1456.0, 1383.9, 1076.7 cm$^{-1}$.

Analysis cacl'd for C$_{19}$H$_{20}$BrN$_5$O: C, 55.08; H, 4.87; N, 16.91; Found: C, 55.59; H, 4.92; N, 16.67.

EXAMPLE 5
(trans)-N-(6-Cyano-1,2,3,4-tetrahydro-3-hydroxy-2,2-dimethyl-4-quinolinyl)-N''-cyano-N'-phenylguanidine

A. 1-Acetyl-6-bromo-3-hydroxy-4-amino-N-acetyl-2,2-dimethyl-1,2,3,4-tetrahydroquinoline A suspension of 1-acetyl-6-bromo-3-hydroxy-4-amino-2,2-dimethyl-1,2,3,4-tetrahydroquinoline (2.6 g, 8.0 mmol, prepared as described in part G of Example 4) in acetic anhydride (30 ml) was treated with sodium acetate (2.4 g) and heated at 90° C. for 3 hours. It was then poured into water and extracted with ethyl acetate (3×150 ml). The combined organic layers were washed with water, dried over magnesium sulfate and concentrated in vacuo. The residue was triturated with isopropyl ether to give the title A compound as a solid (2.0 g). $^1$H NMR (CDCl$_3$) δ 7.31 (s, 1H), 7.18 (dd J=3.0 & 7.0 Hz, 1H), 6.41 (d, J=9.0 Hz, 1H), 5.70 (d, J=9.0 Hz, 1H), 5.36 (t, J=10.0 Hz, 1H), 4.97 (d, J=10.0 Hz, 1H), 2.16 (s, 3H), 2.10 (s, 3H), 1.28 (s, 3H), 1.24 (s, 3H).

B. 1-Acetyl-6-cyano-3-hydroxy-4-amino-N-acetyl-2,2-dimethyl-1,2,3,4-tetrahydroquinoline A solution of the title A compound (2.0 g, 5.6 mmol) and copper(I)cyanide (1.0 g) in N-methylpyrrolidone (15 ml) was heated at 200° C. for 4 hours. After cooling, the mixture was poured into 6N ammonium hydroxide solution (100 ml) and extracted with ethyl acetate (3×150 ml). The combined extracts were washed with water and dried over anhydrous magnesium sulfate. Removal of solvent in vacuo gave the title B compound as an oil (1.6 g). $^1$H NMR (CDCl$_3$) δ 7.26 (s, 1H), 7.16 (d, J=8.0 Hz, 1H), 6.41 (d, J=9.0 Hz, 1H), 6.09 (d, J=10.0 Hz, 1H), 5.18 (t, J=10.0 Hz, 1H), 4.84 (d, J=10.0 Hz, 1H), 4.69 (s, 1H), 2.25 (t, J=8.0 Hz, 1H), 2.04 (s, 3H), 1.99 (s, 3H), 1.18 (s, 3H), 1.13 (s, 3H). $^{13}$C NMR (CDCl$_3$) δ 171.0, 170.8, 146.2, 132.4, 120.0, 119.6, 114.0, 99.2, 75.1, 53.5, 49.3, 48.5, 30.6, 26.9, 23.1, 22.3, 20.7.

C. 6-Cyano-3-hydroxy-4-amino-2,2-dimethyl-1,2,3,4-tetrahydroquinoline

To a solution of the title B compound (1.6 g, 5.3 mmol) in dioxane (15 ml) was added concentrated sulfuric acid (1.6 g) in water (10 ml) and the reaction was heated under reflux for 16 hours. Dioxane was distilled off and the reaction mixture was diluted with water (50 ml), basified to pH 13 with 10N sodium hydroxide and extracted with ethyl acetate (3×150 ml). The combined organic layers were washed with water and dried over anhydrous magnesium sulfate. The solvent was evaporated in vacuo and the residue was triturated with isopropyl ether to give the title C compound as a solid (0.7 g). $^1$H NMR (DMSO-d$_6$) δ 7.58 (s, 1H), 7.17 (dd, J=8.0 Hz, 1H), 6.36 (d, J=9.0 Hz, 1H), 4.5 (s, 1H), 3.55 (d, J=10.0 Hz, 1H), 3.14 (d, J=10.0 Hz, 1H), 1.27 (s, 3H), 1.06 (s, 3H). $^{13}$C NMR (CDCl$_3$) δ 146.3, 131.9, 131.5, 113.2, 76.8, 53.9, 51.8, 27.9, 22.4, 21.9.

D.
(trans)-N-(6-Cyano-1,2,3,4-tetrahydro-3-hydroxy-2,2-dimethyl-4-quinolinyl)-N''-cyano-N'-phenylguanidine The solution of N-cyano-N'-phneylthiourea (0.72 g, 4.1 mmol) and the title C compound (0.68 g, 3.1 mmol) in dimethylformamide (10 mL) under argon was treated with 1-(3-dimethylaminopropyl)-2-ethylcarbodiimide hyrochloride (0.89 g, 4.7 mmol). The reaction was stirred at room temperature for 2 hours and then partitioned between 1N hydrochloric acid and ethyl acetate. The aqueous phase was reextracted with ethyl acetate and the combined extracts were washed with water, sodium bicarbonate and brine. After drying over anhydrous magnesium sulfate, the solvent was evaporated and the residue was triturated with ether to give a colorless solid (1.0 g). It was recrystallized from ethyl acetate to yield the title compound, m.p. 218°-219° C. $^1$H NMR (DMSO-d$_6$) δ 9.32 (s, 1H), 7.67 (d, J=9.0 Hz, 1H), 7.40 (m, 6H), 7.22 (m, 1H), 6.96 (s, 1H), 6.63 (d, J=8.2 Hz, 1H), 5.6 (br s, 2H), 4.91 (t, J=9.0 Hz, 1H), 3.46 (m, 1H), 1.30, 1.13 (s, 3H each). $^{13}$C NMR (DMSO-d$_6$) δ 159.2, 147.5, 137.8, 131.7, 129.0, 124.4, 123.2, 120.2, 117.3, 113.5, 95.4, 54.0, 53.2, 27.1, 21.3. IR(KBr) 3427.7, 2214.4, 2175.8, 1610.7, 1581.7, 1510.4 cm$^{-1}$.

Analysis calc'd for C$_{20}$H$_{20}$N$_6$O.0.4 H$_2$O: C, 65.35; H, 5.70; N, 22.87; Found: C, 65.24; H, 5.45; N, 23.07.

EXAMPLE 6

N-(6-Cyano-3,3-dimethyl-1-indanyl)-N'-phenylurea

A. 5-Amino-1,1-dimethyl-indan-3-one

A solution of 1,1-dimethyl-5-nitro-indan-3-one (6.5 g, 3.17 mmoles, prepared according to part D of Example 1) in methanol (150 ml) containing 5% palladium on carbon (0.75 g) was stirred under hydrogen gas at 15 psi for four hours. The catalyst was filtered and the methanol was recovered under vacuum to obtain a green solid (5.72 g). The reaction product was used in the next step without further purification. $^1$H NMR (CDCl$_3$) δ 7.26 (d, J=8.20 Hz, 1H), 6.95 (m, 2H), 3.82 (broad s, 2H), 2.55 (s, 2H), 1.36 (s, 6H); $^{13}$C NMR (CDCl$_3$) δ 206.25, 154.53, 146.05, 136.27, 124.04, 123.03, 107.14, 53.41, 37.74, 30.04.

B. 5-Cyano-1,1-dimethylindan-3-one

To a solution of the title A compound (5.70 g, 32.5 mmoles) in ethanol (28.5 ml) cooled to 0° C. was added cold dilute aqueous hydrochloric acid solution (7.98 ml concentrated hydrochloric acid in 57 ml water) followed by a solution of sodium nitrite (2.51 g) dissolved in water (17 ml) dropwise until a positive starch-iodide test was obtained. The diazonium salt solution was transferred to a jacketed addition funnel (cooled to 0° C.) and added dropwise to a suspension of KCN (8.44 g, 0.13 mole) and CuCN (11.57 g, 0.13 mole) in water (115 ml) heated to 90° C. The reaction mixture was stirred an additional 25 minutes at 90° C., cooled to room temperature and partitioned between water and diethyl ether. The organic phase was washed with saturated sodium chloride solution, dried over anhydrous magnesium sulfate and evaporated in vacuo to obtain 7.25 g of an orange solid. The crude product ws crystallized from isopropanol to obtain the title B compound as a yellow solid (3.7 g). The residue obtained upon evaporation of the mother liquor (1.54 g) was chromatographed on silica eluting with hexane/acetic acid (4:1) to afford an additional 0.44 g of product for a combined yield of 70.2%. $^1$H NMR (CDCl$_3$) δ 7.98 (s, 1H), 7.87 (d, J=8.21 Hz, 1H), 7.66 (d, J=8.21 Hz, 1H), 2.66 (s, 2H), 1.49 (s, 6H); $^{13}$C NMR (CDCl$_3$) δ 203.42, 167.45, 137.59, 135.89, 127.68, 124.86, 117.95, 111.79, 52.58, 39.16, 29.60; MS: (M+H)$^+$ ~203, M$^-$ ~185.

C. 5-Cyano-1,1-dimethyl-indan-3-ol

To a slurry of the title B compund (3.50 g, 18.89 mmoles) in absolute ethanol (195 ml) cooled to 0° C. was added sodium borohydride (0.72 g, 18.89 mmoles). The reaction mixture was warmed to room temperature and stirred under argon for three hours. The ethanol was recovered under vacuum; the residue was partitioned between ethyl acetate and water. The aqueous phase was extracted with ethyl acetate. The combined organics were washed with saturated sodium chloride solution, dried over anhydrous magnesium sulfate and evaporated in vacuo to obtain 3.66 g of a yellow gum. The crude product was chromatographed on silica eluting with 7:3 hexane/ethyl acetate to obtain the title C compound as a colorless gum (3.15 g). $^1$H NMR (CDCl$_3$) δ 7.66 (s, 1H), 7.58 (d, J=7.63 Hz, 1H), 7.28 (d, J=7.63 Hz, 1H), 5.29 (m, 1H), 2.42 (dd, J=7.04, 12.90 Hz, 1H), 1.88 (dd, J=6.74, 13.20 Hz, 1H), 1.40 (s, 3H), 1.22 (s 3H); $^{13}$C NMR (CDCl$_3$) δ 157.13, 145.01, 132.38, 128.20, 123.15, 119.17, 110.20, 73.22, 51.18, 42.59, 29.32, 29.09; MS: (M+NH$_4$)$^+$ ~205.

D. 3-Chloro-5-Cyano-1,1-dimethylindane

To a solution of the title C compound (3.15 g, 16.82 mmoles) in pyridine (31.5 ml) cooled to 0° C. was added dropwise methanesulfonyl chloride (3.85 g, 33.6 mmoles, 2 eq.). The reaction mixture was warmed to room temperature, stirred under argon for four hours, then partitioned between ethyl acetate and cold dilute (5%) aqueous hydrochloric acid solution. The aqueous phase was extracted with ethyl acetate. The combined organic layers were washed with 5% hydrochloric acid solution, saturated sodium hydrogen carbonate solution, saturated sodium chloride solution, dried over anhydrous magnesium sulfate and evaporated in vacuo to obtain the title D compound as an orange oil (3.01 g) which solidified upon standing. The reaction product was used in the next step without further purification. $^1$H NMR (CDCl$_3$) δ 7.71 (s, 1H), 7.62 (dd, J=1.10, 7.92 Hz, 1H), 7.32 (d, J=7.92 Hz, 1H), 5.40 (dd, J=5.42, 7.13 Hz, 1H), 2.62 (dd, J=7.48, 14.06 Hz, 1H), 2.30 (dd, J=5.22, 13.92 Hz, 1H), 1.46 (s, 3H), 1.30 (s, 3H); $^{13}$C NMR (CDCl$_3$)δ 156.89, 142.96, 133.01, 129.19, 123.45, 118.84, 111.06, 58.61, 51.41, 43.91, 29.20, 28.94; MS: (M+NH$_4$)$^+$ ~223, M$^-$ ~205.

E. 3-Azido-5-cyano-1,1-dimethylindane

A solution of the title D compound (3.0 g, 14.6 mmoles) and sodium azide (1.9 g, 29.2 mmoles, 2 eq.) in N,N-dimethylformamide (30 ml) was stirred under argon at room temperature for 18 hours. The reaction mixture was partitioned between water and ethyl acetate. The aqueous phase was extracted with ethyl acetate. The combined organics were washed with water, 10% sodium carbonate solution, saturated sodium chloride solution, dried over anhydrous magnesium sulfate and evaporated under vacuum to obtain the title E compound as an orange gum (2.14 g). The reaction product was used in the next step without further purification. $^1$H NMR (CDCl$_3$) δ 7.64 (s, 1H), 7.61 (s, 1H), 7.31 (d, J=8.21 Hz, 1H), 4.95 (d, J=6.74 Hz, 1H), 2.40 (dd, J=7.32, 13.20 Hz, 1H), 2.02 (dd, J=6.15, 13.20 Hz, 1H), 1.40 (s, 3H), 1.19 (s, 3H); $^{13}$C NMR (CDCl$_3$) δ 157.14, 140.67, 132.81, 128.06, 123.39, 118.55, 110.58, 62.69, 46.96, 42.53, 28.71; MS: (M+NH$_4$)$^+$~230.

F. 3-Amino-5-cyano-1,1-dimethylindane

A solution of the title E compound (2.14 g, 10.1 mmoles) in ethanol (55 ml) containing 5% palladium on carbon (0.29 g) was stirred under hydrogen gas for three hours at room temperature. The reaction mixture was filtered to remove the catalyst. The filtrate was acidified to pH 1-2 with concentrated hydrochloric acid and concentrated under vacuum to obtain an off-white semi-solid. The crude product was partitioned between water and ethyl acetate. The organic phase was discarded; the aqueous phase was adjusted to pH 11-12 with 50% sodium hydroxide solution and extracted with diethyl ether. The extract was washed with saturated sodium chloride solution, dried over sodium sulfate and evaporated in vacuo to provide the title F compound as a pale green gum. (1.16 g). $^1$H NMR (CDCl$_3$) δ 7.61 (s, 1H), 7.51 (d, J=7.62 Hz, 1H), 7.25 (d, J=7.62 Hz, 1H), 4.42 (d, J=7.92 Hz, 1H), 2.42 (dd, J=7.32, 12.60 Hz, 1H), 1.63 (m, 1H), 1.39 (s, 3H), 1.19 (s, 3H); $^{13}$C NMR (CDCl$_3$) δ 156.62, 147.15, 131.22, 127.05, 122.53, 119.01, 109,89, 53.96, 52.84, 41.92, 28.65, 28.07; MS: (M+H)$^+$~187, (M-H)$^-$~185.

G. N-(6-Cyano-3,3-dimethyl-1-indanyl)-N'-phenylurea

A solution of the title F compound (0.40 g, 2.15 mmol) and phenyl isocyanate (0.26 g, 2.15 mmole) in ethanol (3.5 ml) under argon was heated at reflux for three hours. The solvent was recovered under vacuum and the residue was chromatographed on silica gel eluting with 7:3 hexane/ethyl acetate to obtain a white amorphous solid (0.49 g). This material was further purified by crystallization from isopropyl ether to obtain the title compound as a pure white solid (0.39 g), m.p. 150°-152° C. $^1$H NMR (DMSO-d$_6$) δ 8.47 (s, 1H), 7.73 (d, J=7.62 Hz, 1H), 7.66 (s, 1H), 7.46 (m, 3H), 7.25 (d, J=7.62 Hz, 2H), 6.92 (d, J=7.33 Hz, 1H), 6.62 (d, J=8.20 Hz, 1H), 5.28 (m, 1H), 2.37 (dd, J=7.62, 12.90 Hz, 1H), 1.77 (d, J=8.80 Hz, 1H), 1.38 (s, 3H), 1.21 (s, 3H); $^{13}$C NMR (DMSO-d$_6$) δ 157.05, 155.12, 144.81, 140.26, 132.11, 128.68, 127.73, 123.59, 121.25, 119.06, 117.80, 109.48, 51.88, 48.72, 42.18, 28.64, 28.38.

Analysis calc'd for C$_{19}$H$_{19}$N$_3$O: C, 74.73; H, 6.27; N, 13.76; Found: C, 74.94; H, 6.34; N, 13.65.

EXAMPLE 7

N-(6-Cyano-3,3-dimethyl-1-indanyl)-N'-(phenylmethyl)urea

A solution of 3-amino-5-cyano-1,1-dimethylindane (0.40 g, 2.15 mmol, prepared according to part F of Example 6) and benzyl isocyanate (0.29 g, 2.15 mmole) in ethanol (3.5 ml) under argon was heated at reflux for three hours. The solvent was recovered under vacuum to obtain 0.87 g of yellow gum. The crude product was chromatographed on silica eluting with 1:1 ethyl acetate/hexane to obtain an amorphous white solid (0.44 g). The chromatogrpahy isolate was further purified by crystallization from isopropyl ether to afford the title compound as a pure white solid (0.40 g), m.p. 130°-132° C. $^1$H NMR (d, J=8.21 Hz, 1H), 7.52 (s, 1H), 7.44 (d, J=7.63 Hz, 1H), 7.31 (m, 5H), 6.44 (m, 2H), 5.22 (m, 1H), 4.28 (d, J=5.86, 2H), 2.30 (dd, J=7.04, 12.90 Hz, 1H), 1.71 (dd, J=9.38, 12.31 Hz, 1H), 1.35 (s, 3H), 1.17 (s, 3H); $^{13}$C NMR δ 157.97, 156.88, 145.38, 140.75, 131.88, 128.19, 127.59, 126.98, 126.58, 123.50, 119.06, 109.33, 52.06, 48.74, 42.98, 42.00, 28.64, 28.21.

Analysis calc'd for C$_{20}$H$_{21}$N$_3$O: C, 75.21; H, 6.63; N, 13.16; Found: C, 75.31; H, 6.79; N, 12.95.

EXAMPLE 8

N''-Cyano-N'-(6-cyano-3,3-dimethyl-1-indanyl)-N'-phenylguanidine

A solution of 3-amino-5-cyano-1,1-dimethylindane (0.30 g, 1.58 mmol, prepared according to part F of Example 6), N-cyano-N'-phenylthiourea (0.36 g, 2.05 mmol) and 1-(3-dimethylaminopropyl)-2-ethylcarbodiimide.HCl (0.39 g, 2.05 mmol) in N,N-dimethylformamide (2 ml) was stirred at room temperature for three hours. The reaction mixture was partitioned between 10% citric acid solution and ethyl acetate. The organic fraction was washed with distilled water, saturated sodium hydrogen carbonate solution, saturated sodium chloride solution, dried over anhydrous magnesium sulfate and evaporated in vacuo to obtain 0.54 g of an off-white solid. The crude reaction product was crystallized from the minimum amount of ethanol to provide the title compound as a pure white solid (0.35 g), m.p. 215°-217° C. $^1$H NMR (DMSO-d$_6$) δ 9.25 (s, 1H), 7.73 (m, 2H), 7.62 (d, J=8.79 Hz, 1H), 7.46 (d, J=7.62 Hz, 1H), 7.34 (m, 4H), 7.13 (m, 1H), 5.49 (dd, J=8.21, 16.42 Hz, 1H), 2.34 (dd, J=7.62, 12.31 Hz, 1H), 1.92 (dd, J=9.38, 12.32 Hz, 1H), 1.33 (s, 3H), 1.18 (s, 3H); $^{13}$C NMR (DMSO-d$_6$) δ 158.06, 156.96, 143.48, 137.61, 132.20, 128.94, 127.76, 124.77, 123.70, 123.56, 119.12, 116.96, 109.42, 54.22, 47.65, 42.12, 28.93, 27.87.

Analysis calc'd for C$_{20}$H$_{19}$N$_5$.0.22H$_2$O: C, 72.05; H, 5.88; N, 21.01; Found: C, 72.40; H, 5.92; N, 20.66.

What is claimed is:
1. A compound having the formula

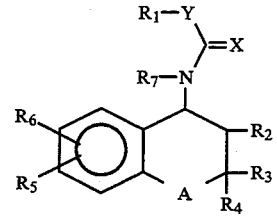

I wherein X is NCN; and A is a single bond or NR$_9$ wherein R$_9$ is alkyl of 1-4 carbons;
Y is —NR$_8$;
R$_1$ is aryl or arylalkyl;
R$_2$ is hydrogen, hydroxy, or

R$_3$ and R$_4$ are each independently hydrogen, alkyl or arylalkyl;
R$_5$ is hydrogen, alkyl, haloalkyl, alkenyl, alkynyl, cycloalkyl, arylalkyl, cycloalkylalkyl, —CN, —NO$_2$, —COR, —COOR, —CONHR, —CONR$_2$, —CF$_3$, S-alkyl, —SOalkyl, —SO$_2$alkyl,

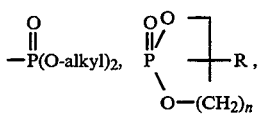

halogen, $OCF_3$, $OCH_2CF_3$, wherein R in each of the above groups is hydrogen, alkyl, aryl, arylalkyl, cycloalkyl, (cycloalkyl)alkyl or haloalkyl;

$R_6$ is hydrogen, alkyl, halo, OH, O-alkyl, amino and substituted amino, as defined hereinbelow, O-alkyl, —OCOalkyl, —OCONRalkyl, —NRCOalkyl, and NRCOOalkyl, $NRCONR_2$ wherein R in each of the above groups is hydrogen, alkyl, aryl, arylalkyl, cycloalkyl, (cycloalkyl)alkyl or haloalkyl;

$R_7$ and $R_8$ are each independently hydrogen, alkyl, or arylaklyl;

or $R_1$ and $R_8$, or $R_1$ and $R_7$ or $R_7$ and $R_8$ taken together can form a 5- to 7-membered ring, which may further include an aryl group fused to 2 carbon atoms of such 5- to 7-membered ring;

n is 1, 2 or 3; and, $R_{10}$ is hydrogen, hydroxy, alkyl or O-alkyl; and further wherein the term "alkyl" refers to straight or branched chain saturated hydrocarbon radicals having up to eight carbons; the terms "alkoxy" and "alkylthio" refer to such alkyl groups attached to an oxygen or sulfur;

the term "alkenyl" refers to straight or branched chain hydrocarbon radicals having from two to eight carbons and one double bond; the term "alkynyl" refers to straight or branched chain hydrocarbon radicals having from two to eight carbons and one triple bond;

the term "cycloalkyl" refers to saturated carbocyclic rings of 3 to 7 carbon atoms;

the term "halo" or "halogen" refers to chloro, bromo, iodo and fluoro;

the term "halo substituted alkyl" refers to such alkyl groups described above in which one or more hydrogens have been replaced by chloro, bromo or fluoro groups;

the term "aryl" refers to phenyl, 1-naphthyl, 2-naphthyl or mono substituted phenyl, 1-naphthyl, 2-naphthyl wherein said substituent is alkyl of 1 to 4 carbons, alkylthio of 1 to 4 carbons, alkoxy of 1 to 4 carbons, halo, nitro, cyano hydroxy, amino, —NH-alkyl wherein alkyl is of 1 to 4 carbons, —N(alkyl)$_2$ wherein alkyl is of 1 to 4 carbons, $N(R_{11})COR_{11}'$, $N(R_{11})CO$-haloalkyl, $N(R_{11})CO$-amino, $N(R_{11})CO$-substituted amino, $COR_{11}$, $COOR_{11}$ (wherein $R_{11}$ and $R_{11}'$ are independently H, alkyl, haloalkyl, aryl, arylalkyl) —$CF_3$, —$OCHF_2$,

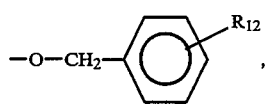

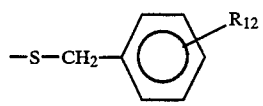

(wherein $R_{12}$ is hydrogen, alkyl of 1 to 4 carbons, alkoxy of 1 to 4 carbons, alkylthio of 1 to 4 carbons, halo, hydroxy or $CF_3$), —O—$CH_2$-cycloalkyl, or —S—$CH_2$-cycloalkyl, and di-substituted phenyl, 1-naphthyl, 2-naphthyl wherein said substituents are selected from methyl, methoxy, methylthio, halo, $CF_3$, nitro, amino, and $OCHF_2$;

the term "substituted amino" refers to a group of the formula —$NZ_1Z_2$ wherein $Z_1$ is hydrogen, alkyl, cycloalkyl, aryl, arylalkyl or cycloalkylalkyl and $Z_2$ is alkyl, cycloalkyl, aryl, arylalkyl or cycloalkylalkyl.

2. A compound of claim 1 wherein
A is a single bond, or $CH_2$;
$R_1$ is aryl, or arylmethyl;
$R_2$ is hydrogen, or trans-OH;
$R_3$ and $R_4$ are each methyl;
$R_5$ is hydrogen;
$R_6$ is CN, or $NO_2$;
$R_7$ is hydrogen;
X is NCN;
Y is $NR_8$; and,
$R_8$ is hydrogen.

3. A compound of claim 1 wherein
A is a single bond;
$R_1$ is phenyl, or phenylmethyl;
$R_2$ is trans-OH;
$R_3$ and $R_4$ are each methyl;
$R_5$ is hydrogen;
$R_6$ is CN, or $NO_2$;
$R_7$ is hydrogen;
X is NCN;
Y is $NR_8$; and,
$R_8$ is hydrogen.

4. A compound of claim 1 having the name (trans)-N"-cyano-N-(2-hydroxy-3,3-dimethyl-6-nitro-1-indanyl)-N'-phenylguanidine.

5. A compound of claim 1 having the name (trans-)N-(2-hydroxy-3,3-dimethyl-6-nitro-1-indanyl)-N'-phenylurea.

6. A compound of claim 1 having the name (trans)-N-(2-hydroxy-3,3-dimethyl-6-nitro-1-indanyl)-N'-(phenylmethyl)urea.

7. A compound of claim 1 having the name (trans)-N-(6-bromo-1,2,3,4-tetrahydro-3-hydroxy-2,2-dimethyl-4-quinolinyl)-N"-cyano-N'-phenylguanidine.

8. A compound of claim 1 having the name (trans)-N-(6-cyano-1,2,3,4-tetrahydro-3-hydroxy-2,2-dimethyl-4-quinolinyl)-N"-cyano-N'-phenylguanidine.

9. A compound of claim 1 having the name N-(6-cyano-3,3-dimethyl-1-indanyl)-N'-phenylurea.

10. A compound of claim 1 having the name N-(6-cyano-3,3-dimethyl-1-indanyl)-N'-(phenylmethyl)urea.

11. A compound of claim 1 having the name N"-cyano-N'-(6-cyano-3,3-dimethyl-1-indanyl)-N'-phenylguanidine.

* * * * *